(12) United States Patent
Walser et al.

(10) Patent No.: US 11,305,112 B2
(45) Date of Patent: Apr. 19, 2022

(54) ELECTRICAL STIMULATION IMPLANTS

(71) Applicant: DePuy Synthes Products, Inc., Raynham, MA (US)

(72) Inventors: Jochen Walser, Ostermundigen (CH); Mario Gehri, Aarberg/BE (CH); Andre Furrer, Luterkofen (CH)

(73) Assignee: DePuy Synthes Products, Inc., Raynham, MA (US)

( * ) Notice: Subject to any disclaimer, the term of this patent is extended or adjusted under 35 U.S.C. 154(b) by 20 days.

(21) Appl. No.: 15/980,972

(22) Filed: May 16, 2018

(65) Prior Publication Data

US 2019/0351223 A1 Nov. 21, 2019

(51) Int. Cl.
*A61B 17/80* (2006.01)
*A61B 17/86* (2006.01)
(Continued)

(52) U.S. Cl.
CPC .......... *A61N 1/326* (2013.01); *A61B 17/8057* (2013.01); *A61B 17/8605* (2013.01); *A61N 1/05* (2013.01); *A61B 2017/00526* (2013.01); *A61B 2017/00876* (2013.01); *A61B 2017/00929* (2013.01); *A61C 8/0007* (2013.01);
(Continued)

(58) Field of Classification Search
CPC ..... A61B 17/68; A61B 17/16; A61B 17/8057; A61B 17/8052; A61B 17/80; A61B 17/8605; A61B 17/8625; A61B 17/86; A61B 2018/0071; A61B 2018/00876; A61B 2018/00929; A61B 5/0422; A61B 5/053; A61B 2017/00876; A61B 2017/00929; A61N 1/326; A61N 1/40; A61N 1/205; A61N 1/05; A61N 2/02; A61N 2/002; A61N 2/00; A61N 2/004;
(Continued)

(56) References Cited

U.S. PATENT DOCUMENTS 4,216,548 A 8/1980 Kraus
4,306,564 A 12/1981 Kraus
(Continued)

FOREIGN PATENT DOCUMENTS

CA 1216634 A 1/1987
DE 2116869 A1 10/1971
(Continued)

*Primary Examiner* — Marcela I. Shirsat
(74) *Attorney, Agent, or Firm* — BakerHostetler (57) ABSTRACT

A bone implant kit includes an implant and first and second electrical stimulation anchors. The implant defines an inner surface inner configured to face a bone to which the bone implant kit is configured to attach, and an outer surface opposite the inner surface. The implant further defines first and second bone fixation holes that each extend from the inner surface to the outer surface. The first and second bone fixation holes are spaced from each other along a longitudinal direction. The first electrical stimulation anchor can be sized and configured for insertion into the first bone fixation hole, and the second electrical stimulation anchor can be sized and configured for insertion into the second bone fixation hole. The first and second electrical stimulation anchors can be configured to respond to a magnetic field so as to generate an electric field between the first and second electrical stimulated anchors.

20 Claims, 7 Drawing Sheets

(51) Int. Cl.
*A61N 1/05* (2006.01)
*A61B 17/00* (2006.01)
*A61N 2/00* (2006.01)
*A61N 1/20* (2006.01)
*A61C 8/02* (2006.01)
*A61N 1/32* (2006.01)

(52) U.S. Cl.
CPC ............ *A61N 1/0551* (2013.01); *A61N 1/205* (2013.01); *A61N 2/006* (2013.01)

(58) Field of Classification Search
CPC .... A61N 2/006; A61N 1/0551; A61C 8/0006; A61C 8/0007
USPC ....... 606/291, 300, 301, 304, 309, 279, 275; 600/547, 546, 554, 372–375; 411/381, 411/382, 383, 395, 424; 607/50–51
See application file for complete search history.

(56) References Cited

U.S. PATENT DOCUMENTS

| | | | |
|---|---|---|---|
| 4,421,115 A | | 12/1983 | Kraus |
| 5,292,252 A | * | 3/1994 | Nickerson .............. A61C 8/008 433/173 |
| 5,709,686 A | * | 1/1998 | Talos ................. A61B 17/8014 606/280 |
| 6,034,295 A | * | 3/2000 | Rehberg ................ A61F 2/3662 623/23.49 |
| 6,120,502 A | | 9/2000 | Michelson |
| 6,778,861 B1 | * | 8/2004 | Liebrecht ................ A61B 17/86 606/304 |
| 7,890,179 B2 | | 2/2011 | Wiegmann et al. |
| 8,348,983 B2 | * | 1/2013 | Neubardt ........... A61B 17/8625 606/304 |
| 8,380,319 B2 | | 2/2013 | Berger |
| 8,425,395 B2 | | 4/2013 | Kraus et al. |
| 9,327,115 B2 | | 5/2016 | Neuman et al. |
| 9,474,900 B2 | | 10/2016 | Werner |
| 9,474,908 B2 | | 10/2016 | Hirschl |
| 9,776,014 B2 | | 10/2017 | Neuman et al. |
| 9,844,662 B2 | | 12/2017 | Leuthardt et al. |
| 2007/0179493 A1 | | 8/2007 | Kim |
| 2009/0099404 A1 | * | 4/2009 | Kraus .................... A61B 17/86 600/13 |
| 2010/0036467 A1 | | 2/2010 | Kraus et al. |
| 2010/0143871 A1 | | 6/2010 | Berger |
| 2010/0292756 A1 | | 11/2010 | Schneider |
| 2014/0257420 A1 | | 9/2014 | Fox |
| 2015/0080636 A1 | | 3/2015 | Rogachefsky et al. |
| 2017/0093357 A1 | * | 3/2017 | Okada .................. H05K 9/0071 |
| 2018/0110552 A1 | * | 4/2018 | Park .................... A61B 17/8685 |

FOREIGN PATENT DOCUMENTS

| | | |
|---|---|---|
| EP | 1854503 A1 | 11/2007 |
| EP | 2050482 A1 | 4/2009 |
| EP | 2074958 A2 | 7/2009 |
| EP | 2361589 A1 | 8/2011 |
| EP | 2836267 A1 | 2/2015 |
| EP | 3030312 A1 | 6/2016 |
| GB | 1393702 A | 5/1975 |
| WO | 2007/023320 A1 | 3/2007 |
| WO | 2013/155093 A1 | 10/2013 |
| WO | 2013/164824 A1 | 11/2013 |
| WO | 2015/076698 A1 | 5/2015 |
| WO | 2016/169578 A1 | 10/2016 |

* cited by examiner

ELECTRICAL STIMULATION IMPLANTS

TECHNICAL FIELD

This disclosure relates generally to bone fixation implants, and in particular relates to implants that can perform electromagnetic stimulation of a bone fracture to improve healing of the bone fracture.

BACKGROUND

When bones are damaged through trauma, disease, distraction osteogenesis, or orthognathic surgery, bone fixation implants are commonly used to provide anatomical reduction of bone fragments, to maintain their position, and to ensure union in the desired position. Thus, bone fixation implants are typically designed to achieve proper anatomic fit and function. Additionally, because bone fixation implants often support bones that withstand significant mechanical stress in their anatomic function, implants are often composed of strong and rigid materials. Intramedullary nails are example implants that are commonly used to treat fractures in long bones of the body such as fractures in femurs, tibias, and humeri. To treat such fractures, the intramedullary nail is inserted into a medullary canal of the long bone such that the nail spans across one or more fractures to fragments of the long bone that are separated by the one or more fractures. Bone anchors are then inserted through the bone and into the intramedullary, thereby fixing the intramedullary nail to the bone. The intramedullary nail can remain in the medullary canal at least until the fracture is fused.

SUMMARY

In an example, a bone implant kit includes an implant and first and second electrical stimulation anchors. The implant define an inner surface configured to face a bone to which the bone implant kit is configured to be attached, and an outer surface opposite the inner surface. The implant further defines first and second bone fixation holes that each extend from the inner surface to the outer surface. The implant can define a first internal surface that extends from the inner surface to the outer surface so as to define the first bone fixation hole, and a second internal surface that extends from the inner surface to the outer surface so as to define the second bone fixation hole. The first and second bone fixation holes are spaced from each other along a longitudinal direction. The first electrical stimulation anchor can be sized and configured for insertion into the first bone fixation hole so as to threadedly mate with the first internal surface, and the second electrical stimulation anchor can be sized and configured for insertion into the second bone fixation hole so as to threadedly mate with the second internal surface. The first electrical stimulation anchor can include a first electrical coil wound around a first ferromagnetic core in a first direction, and the second electrical stimulation anchor can include a second electrical coil wound around a second ferromagnetic core in a second direction opposite the first direction. The first and second electrical stimulated anchors are configured to secure the implant to the bone such that the inner surface of the implant is spaced from the bone, and the first and second electrical stimulation anchors are configured to respond to a magnetic field so as to generate an electric field between the first and second electrical stimulated anchors.

In another example, an electrical stimulation anchor is configured to lock to a bone implant so as to secure the bone implant to a bone. The electrical stimulation anchor can include a head configured to lock to the bone implant, a tip opposite the head along the central anchor axis, and a shaft that connects the head to the tip. The head can define a first electrode that defines a first electrically conductive outer surface. The shaft can be elongate along the central anchor axis, and the shaft and the tip can define a second electrode that defines a second electrically conductive outer surface. Further, the electrical stimulation anchor can include an electrical insulator that defines a non-conductive outer surface disposed between the first electrically conductive outer surface and the second electrically conductive surface along the central anchor axis so as to separate the first electrode and the second electrode from each other. The non-conductive outer surface can be disposed closer to the head along the central anchor axis as compared to the tip. For example, the non-conductive outer surface can be disposed proximate to the head 112, and can extend around the central anchor axis. Further, the electrical stimulation anchor can include a ferromagnetic core disposed within the electrical insulator, and an electrical coil wound around the ferromagnetic core. The ferromagnetic core can define a core body and a core proximal end that is attached to the head so as to be configured to transfer torque applied to the head about the central anchor axis, to the shaft.

In another example, an electrical stimulation locking anchor is fabricated by winding an electric coil around a ferromagnetic core to define an electrical coil assembly. The electrical coil assembly is inserted into a cavity defined by a shaft body of the electrical stimulation anchor. A proximal end of a ferromagnetic core is attached to the head of the electrical stimulation anchor, and a distal end of the ferromagnetic core is attached to a tip of the electrical stimulation anchor that is opposite the head along a central anchor axis. The shaft body can be secured to the electrical coil, such that electrical current can be transferred between the electrical coil and the shaft body. In an example, the electrical coil assembly that is attached to the head and tip is set in a form, such that the head and the shaft body define a gap therebetween along the central anchor axis. A non-conductive polymer can be injected into a cavity defined by the by the head or the tip, such that the polymer surrounds the electrical coil assembly and fills the gap between the head and shaft body, so as to define an electrical insulator of the electrical stimulation anchor.

In yet another example, a fracture in a bone is treated by positioning a bone plate over the bone, such that the fracture is disposed between a first bone fixation hole and a second bone fixation hole along a longitudinal direction. The method of treating the fracture includes inserting a first electrical stimulation anchor into the first bone fixation hole, and inserting a second electrical stimulation anchor into the second bone fixation hole. The method of treating the fracture further includes causing an electrical field to be generated between the first and second electrical stimulation anchors. Causing the electrical field to be generated can include exposing the bone plate to a magnetic field, so as to induce an electrical current in the first electrical stimulation anchor and the second electrical stimulation anchor.

The foregoing summarizes only a few aspects of the present disclosure and is not intended to be reflective of the full scope of the present disclosure. Additional features and advantages of the disclosure are set forth in the following description, may be apparent from the description, or may be learned by practicing the invention. Moreover, both the foregoing summary and following detailed description are exemplary and explanatory and are intended to provide further explanation of the disclosure.

BRIEF DESCRIPTION OF THE DRAWINGS

The foregoing summary, as well as the following detailed description of example embodiments of the present disclosure, will be better understood when read in conjunction with the appended drawings. For the purposes of illustrating the example embodiments of the present disclosure, references to the drawings are made. It should be understood, however, that the application is not limited to the precise arrangements and instrumentalities shown. In the drawings:

FIG. 1 depicts an example embodiment of an electrical stimulation system that includes a pulsed electromagnetic field (PEMF) device and a bone implant system configured to be attached to a bone, wherein FIG. 1 shows a cross section view of the PEMF device and a perspective view of the bone implant system.

DETAILED DESCRIPTION

As an initial matter, aspects of the disclosure will now be described in detail with reference to the drawings, wherein like reference numbers refer to like elements throughout, unless specified otherwise. Certain terminology is used in the following description for convenience only, and is not limiting. The term "plurality", as used herein, means more than one. The terms "a portion" and "at least a portion" of a structure include the entirety of the structure. Certain features of the disclosure that are described herein in the context of separate embodiments may also be provided in combination in a single embodiment. Conversely, various features of the disclosure that are described in the context of a single embodiment may also be provided separately or in any subcombination.

Figure 1:
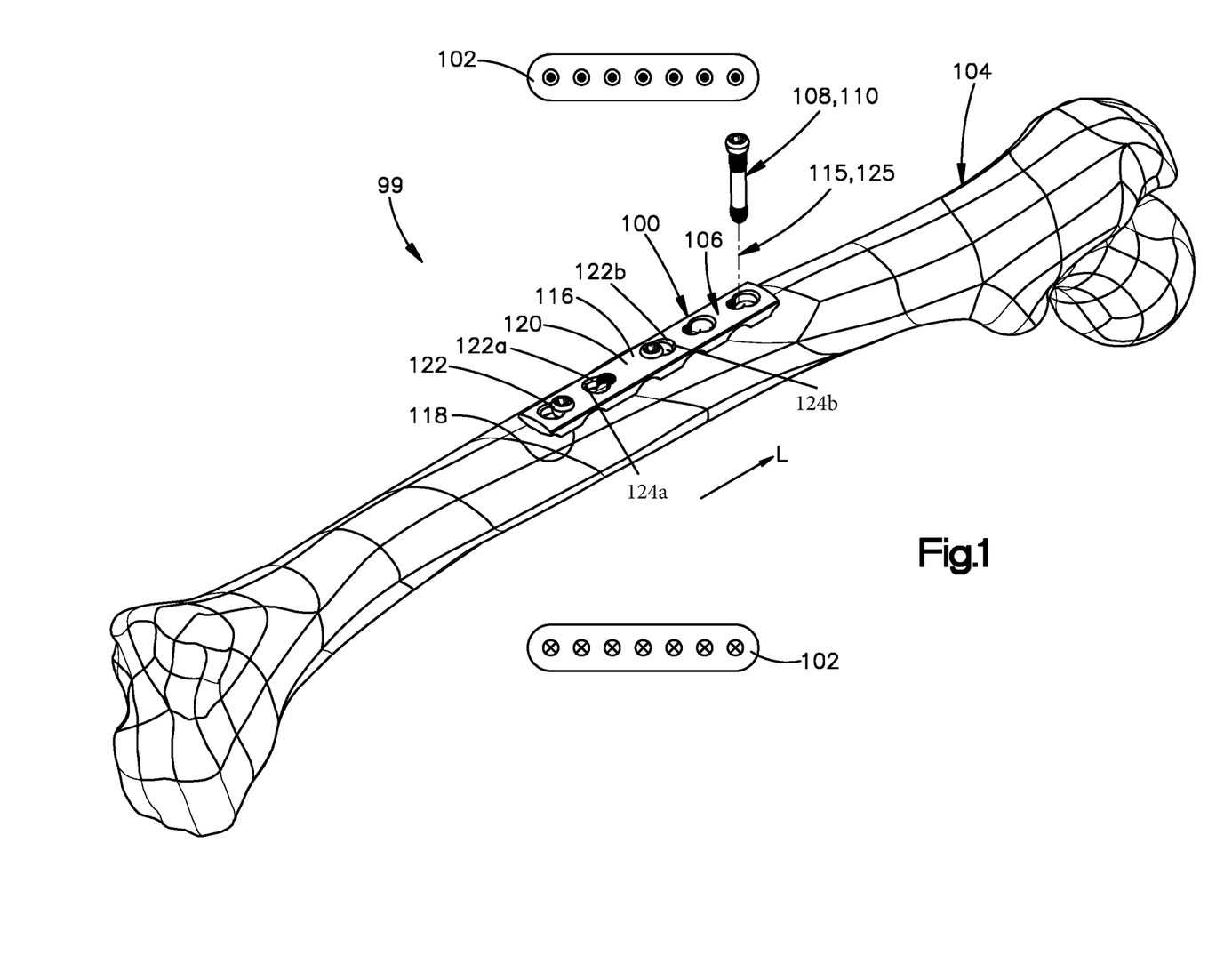
Figure 2:
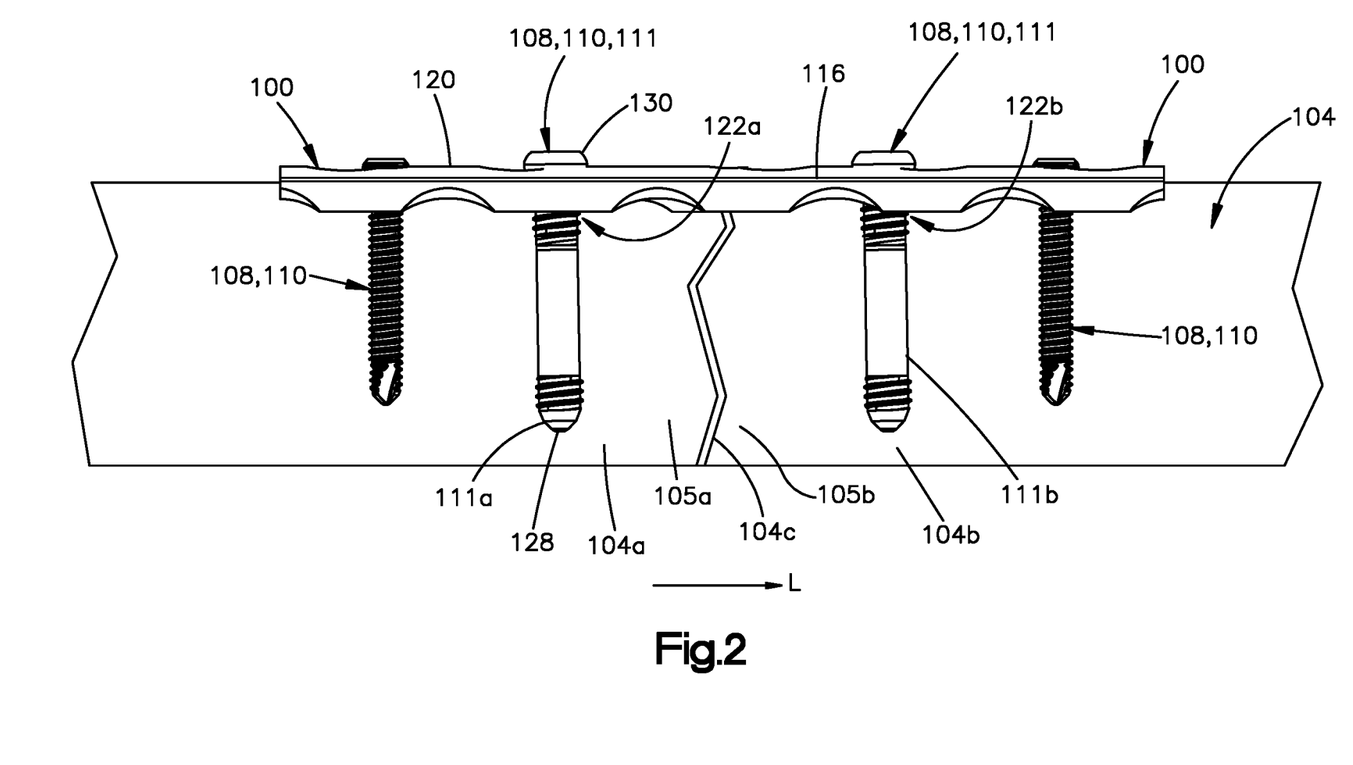
FIG. 2 is a cross section view of a portion of the bone shown in FIG. 1 that includes a fractured portion, wherein the bone implant system attached to the bone includes a bone implant and electrical stimulation anchors disposed on opposite sides of the fractured portion of the bone.

Referring to FIG. 1, an electrical stimulation system 99 includes a bone implant kit or system 100 and a pulsed electromagnetic field (PEMF) device 102. Referring also to FIG. 2, the bone implant system 100 can be configured to be implanted and secured to a bone 104 so as to treat a fractured portion 104c of the bone 104. The bone implant system 100 can be implanted and secured to the bone 104 so as to stabilize a first bone segment 104a of the bone 104 with respect to a second bone segment 104b of the bone 104. The first bone segment 104a and the second bone segment 104b can be separated from each other by the fractured portion 104c of the bone 104. It will be appreciated that the bone 104 can be any bone in the human or animal anatomy suitable for bone implants. Further, while the bone 104 is illustrated having the first bone segment 104a and the second bone segment 104b on opposite sides of the fractured portion 104c, it will be understood that the bone 104 can define any number of fractured portions or bone segments as desired that are configured for fixation using the bone implant system 100.

The bone implant system 100 can include an implant 106, for instance a bone plate or nail, and a plurality of bone anchors 108 that are configured to secure the implant 106 to the underlying bone 104, and in particular to each of the first and second bone segments 104a and 104b. Alternatively, in accordance with another example, the bone implant system 100 includes only the plurality of bone anchors 108, such that the bone anchors 108 are configured to purchase in the bone 104 without the implant 106. The bone anchors 108 can be configured as bone pins or bone screws 110. For purposes of example, the bone anchors 108 are illustrated and often described as bone screws 110, though it will be understood that the bone anchors 108 can be alternatively configured so as to insert into the bone 104, and all such alternatives are contemplated as being within the scope of this disclosure.

Referring to FIGS. 3A to 4D, the bone anchors 108 can include a head 112 and a shaft 114 that extends out with respect to the head 112 along a central anchor axis 125. The shaft 114 can extend directly from the head 112, or can extend from a neck that is disposed between the head 112 and the shaft 114. The shaft 114 can be threaded, such that the bone anchor 108 is configured as the bone screw 110 whose shaft 114 extends out relative to the head 112 along the central anchor axis 125, which can also be referred to as a central screw axis. The threaded shaft 114 can be configured to threadedly purchase in the underlying bone 104. For instance, one or more up to all of the bone screw 110 can be configured as a cortical screw whose threaded shaft 114 is designed and configured to threadedly mate to cortical bone. Alternatively or additionally, one or more of the bone screws 110 can be configured as a cancellous screw whose threaded shaft 114 is designed and configured to threadedly mate to cancellous bone. It is appreciated that cancellous bone screws have threads that have a greater pitch than threads of cortical bone screws. Further, the threads of cancellous bone screws typically extend out from the shaft 114 of the bone screw 110 a greater radial distance than the threads of cortical bone screws.

Figure 3A:
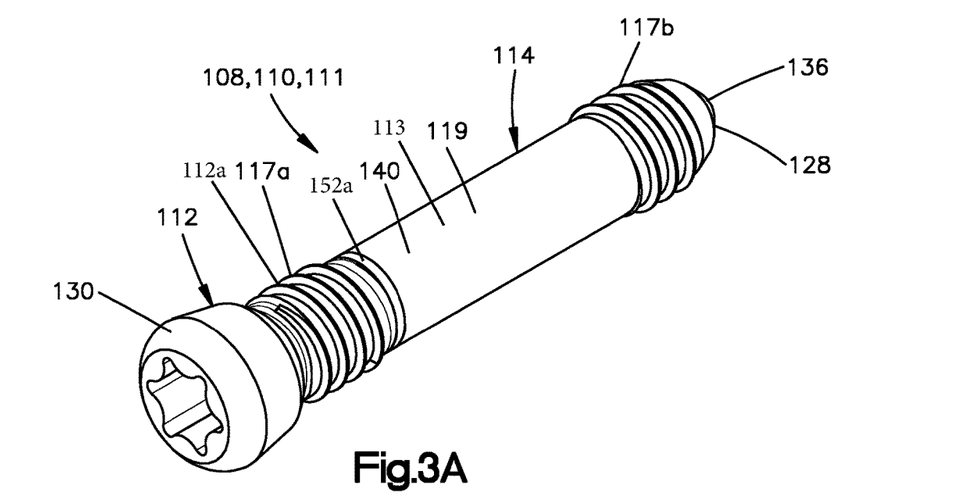
FIG. 3A is a perspective view of the electrical stimulation anchor in accordance with an example embodiment.
Figure 3B:
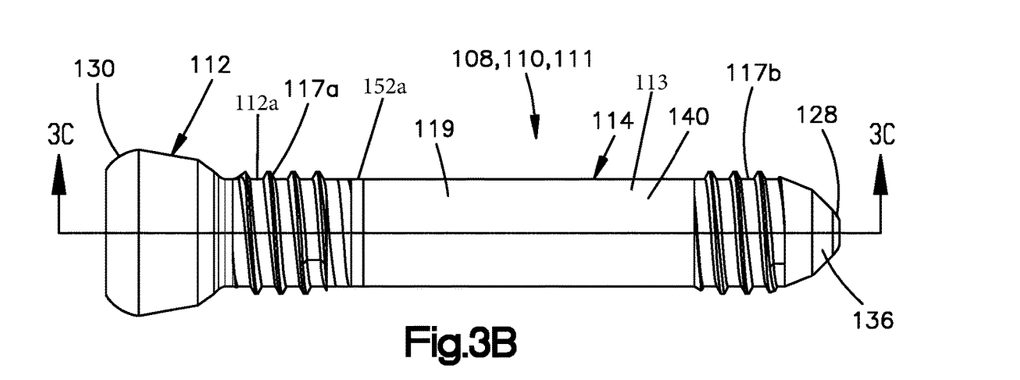
FIG. 3B is a side elevation view of the electrical stimulation anchor depicted in FIG. 3A.

Referring in particular to FIGS. 3A and 3B, in accordance with an example, the shaft 114 can define a first threaded portion 117a, a second threaded portion 117b, and an unthreaded portion 119 between the first and second threaded portions 117a and 117b along the central anchor axis 125. Thus, the shaft 114 of the bone screw 110 can be threaded so as to define a thread that is not continuous from one end of the shaft 114 to the other end of the shaft 114. Alternatively, referring to FIGS. 4A and 4B, the shaft 114 can define a threaded portion 117 having a thread that is continuous from one end of the shaft 114 to the other end of the shaft 114. In an example, as shown, the head 112 can define the first threaded portion 117a. Thus, the head 112 can be configured to lock to the implant 106.

The bone implant system 100 can include one or more for instance two, bone anchors 108 that are configured as electrical stimulation anchors 111. Further, the bone screws 110 can be configured as electrical stimulation anchors 111 configured to secure the implant 106 to the bone 104. In an example configuration, the bone implant system 100 includes a first electrical stimulation locking anchor 111a adjacent to a first side 105a of the fractured portion 104c, and a second electrical stimulation locking anchor 111b adjacent to a second side 105b of the fractured portion 104c that is opposite the first side 105a of the fractured portion 104c. Thus, the first electrical stimulation locking anchor 111a can be inserted into the first bone segment 104a, and the second electrical stimulation locking anchor 111b can be inserted into the second bone segment 104b, such that the fractured portion 104c is between the first and second electrical stimulation locking anchors 111a and 111b along a longitudinal direction L. The first and second electrical stimulation locking anchors 111a and 111b can be configured to secure the implant 106 to the bone 104, and to respond to a magnetic field so as to generate an electric field between the first and second electrical stimulation locking anchors 111a and 111b. In particular, the first and second electrical stimulation locking anchors 111a and 111b can be configured to respond to a magnetic field so as to generate the electric field at the fractured portion 104c of the bone 104, so as to treat, for instance heal, the fractured portion 104c of the bone 104.

Referring now to FIGS. 1 and 2, the implant 106 can include a body or bone plate 116 that defines an inner plate surface 118 configured to face the underlying bone 104 to which the bone implant system 100 is configured to be attached, and an outer plate surface 120 that is opposite the inner plate surface 118. The implant 106 can further define a plurality of bone fixation holes 122 that extend through the plate 116 from the inner plate surface 118 to the outer plate surface 120. In particular, the plate 116, and thus the implant 106, includes a plurality of internal surfaces 124 that each extend from the outer plate surface 120 to the inner plate surface 118 so as to each define a respective one of the bone fixation holes 122. Each of the bone fixation holes 122 can extend from the outer plate surface 120 to the inner plate surface 118 along a central hole axis 115. The central hole axis 115 can be oriented normal to each of the inner plate surface 118 and the outer plate surface 120. It should be appreciated, of course, that the central hole axis 115 of any of the bone fixation holes 122 can be oriented at an oblique angle with respect to the inner plate surface 118 and outer plate surface 120 as desired.

During a surgical procedure using the bone implant system 100, the shaft 114 of the bone anchor 108, for instance the electrical stimulation anchor 111, can be inserted through a respective one of the bone fixation holes 122 and into the underlying bone 104. The electrical stimulation anchor 111 can then be rotated, for example about the central anchor axis 125, so as to cause the threaded shaft 114 to be driven into the underlying bone 104 as the threaded shaft 114 threadedly purchases with the underlying bone 104. The threaded shaft 114 can be driven into the underlying bone 104 until the head 112 engages the implant 106. Alternatively, in an example configuration in which the bone implant system 100 does not include the implant 106, such that the electrical stimulation anchors 111 are configured as standalone screws, the threaded shaft 114 can be driven into the underlying bone 104 until the head 112 engages the underlying bone 104.

One or more up to all of the electrical stimulation anchors 111 can be configured as a compression screw whose head 112 is configured to bear against the implant 106 so as to apply a compressive force against the implant 106 toward the underlying bone 104 when the shaft 114 is driven further into the underlying bone 104 after the head 112 has contacted the outer plate surface 120. The shaft 114 can be driven into the underlying bone a sufficient distance until the desired compressive force has been imparted onto the implant 106. The head 112 of the compression screw can be unthreaded. Similarly, at least a portion up to an entirety of the internal surface 124 can be unthreaded.

In another example, one or more up to all of the electrical stimulation anchors 111 can be configured as locking screws that are configured to lock to the implant 106. Therefore, unless otherwise specified, the electrical stimulation anchors 111 can also be referred to as electrical stimulation locking anchors 111. In particular, the head 112 can be externally threaded. The internal surface 124 can be similarly threaded so as to be configured to threadedly mate with the threaded head 112. Accordingly, during operation, the shaft 114 can be inserted through the fixation hole 122 and driven into the underlying bone 104 as described above. In particular, when the electrical stimulation anchor 111 is a locking screw, rotation of the anchor 111 causes the threaded head 112 to threadedly mate with the internal surface 124. As a result, the screw head 112 fastens the implant 106 to the underlying bone 104 without applying a compressive force onto the implant 106 against the underlying bone 104. The implant 106 can be spaced from the underlying bone 104 when locked to the head 112. Alternatively, the implant 106 can abut the underlying bone 104 when locked to the head 112. At least a portion of the internal surface 124 can be tapered so as to extend in an axially inward direction, for example toward the central hole axis 115, as the internal surface 124 extends from the outer plate surface 120 toward the inner plate surface 118. Thus, the internal surface 124 can be configured to prevent the head 112 from passing completely through the fixation hole 122. The head 112 can define at least one external thread that is circumferentially continuous about the central anchor axis 125. It should be appreciated, however, that the head 112 can be alternatively constructed in any manner desired so as to threadedly mate with the internal surface 124 as described herein.

According to one embodiment, one or more of the fixation holes 122 of the bone implant 106 can be configured as a variable angle locking hole that is configured to threadedly mate with the bone screw 110 at different orientations of the bone screw 110 with respect to the central hole axis 115. That is, when the fixation hole 122 is configured as a variable angle locking hole, the plate 116, and thus the implant 106, includes at least one thread that projects out from the internal surface 124 into the fixation hole 122.

The bone screw 110 can be configured to be inserted into the fixation hole 122 such that the central anchor axis 125 is at one of a plurality of orientations with respect to the central hole axis 115 within a range of orientations at which the threaded head 112 is configured to threadedly mate with the at least one thread in the fixation hole 122. For instance, the bone screw 110 can be configured to be inserted into the fixation hole 122 such that the central anchor axis 125 is at one of a plurality of angles within a range of angles defined by the central anchor axis 125 and the central hole axis 115 at which the threaded head 112 is configured to threadedly mate with the at least one thread in the fixation hole 122. The range of angles can be from approximately zero degrees to approximately thirty degrees. Thus, the range of angles can define a cone of up to approximately sixty degrees. The central anchor axis 125 can be coincident with the central hole axis 115 in one of the orientations in the range of orientations. The at least one thread in the fixation hole 122 and the threads of the head 112 can be defined prior to insertion of the bone screw 110 into the variable angle locking hole. That is, the internal surface 124 can be designed or configured such that threads are not cut into the bone screw head 112. Similarly, the bone screw head 112 can be designed or configured so as to cut no threads into the internal surface 124.

Referring generally to FIGS. 1 and 2, one or more of the anchors 108 in the bone implant system 100, for instance two of the bone anchors 108 in the bone implant system 100, can be configured as electrical simulation implants, such as an electrical stimulation pin or the first electrical stimulation anchor 111a and the second electrical stimulation anchor 111b. For example, the bone fixation holes 122 can include first and second bone fixation holes 122a and 122b, respectively, which are spaced from each other along the longitudinal direction L. A first internal surface 124a can extend from the inner plate surface 118 to the outer plate surface 120 so as to define the first bone fixation hole 122a, and a second internal surface 124b can extend from the inner plate surface 118 to the outer plate surface 120b so as to define the second bone fixation hole 122b. The first electrical stimulation locking anchor 111a can be sized and configured for insertion into the first bone fixation hole 122a so as to threadedly mate with the first internal surface 124a, and the second electrical stimulation locking anchor 111b can be sized and configured for insertion into the second bone fixation hole 122b so as to threadedly mate with the second internal surface 124b. Thus, the first and second electrical stimulation anchors 111a and 111b can be configured to secure the implant 106 to the bone 104 such that the inner plate surface 118 is spaced from the bone 104.

In an example configuration, the first and second electrical stimulation anchors 111a and 111b are substantially the same size as each other, and thus the first and second bone fixation holes 122a and 122b can be substantially the same size as each other. The first and second bone fixation holes 122a and 122b can each extend from the inner plate surface 118 to the outer plate surface 120. The first and second bone fixation holes 122a and 122b can configured to be spaced from each other along the longitudinal direction L such that the fractured portion 104c of the bone 104 to which the bone implant system (kit) 100 is configured to be attached is disposed between the first and second bone fixation holes along the longitudinal direction L when the implant 106 is positioned over the bone. The first and second bone fixation holes 122a and 122b can be adjacent to each other such that no bone fixation holes 122 are between the first and second bone fixation holes along the longitudinal direction L. It will be understood that the bone fixation holes, and thus the electrical stimulation anchors, can be alternatively located, and the location of bone fixation holes and the electrical stimulation anchors may depend on the size and shape of the fracture being treated.

Referring again to FIGS. 3A-4D, the electrical stimulation anchors 111, for instance the electrical stimulation anchors 111a and 111b, can each define a distal end 128 and a proximal end 130 that is opposite the distal end 128 along the central anchor axis 125, such that each of the electrical stimulation anchors 111 are elongate along the central anchor axis 125. The head 112 can be disposed at the proximal end 130. Thus, the proximal end 130 can be configured to be disposed adjacent to the outer plate surface 120 of the implant 106 when the implant 106 is secured to the bone 104. The head 112, and thus the proximal end 130, can define a first electrode 132 of the electrical stimulation anchor 111 that is configured to contact the implant 106 when the implant 106 is secured to the bone 104. The first electrode, and thus the head, can define a first electrically conductive outer surface 112a configured to contact the implant 106 when the implant 106 is secured to the bone 104. The distal end 128 can be considered to be an insertion end or leading end, and can define a second electrode 134 of the electrical stimulation anchor 111. The second electrode 134 can include a second electrically conductive outer surface 113 electrically isolated from the first electrically conductive outer surface 112a, such that electrical current induced by a magnetic field is not transferred from the first electrode 132 to the second electrode 134. The shaft 114 can extend between the proximal end 130 and the distal end 128 along the central anchor axis 125 so as to be elongate along the central anchor axis 125. With particular reference to FIGS. 3A and 3B, the shaft 114 can define the first threaded portion 117a that can be adjacent to the proximal end 130. In an example, the shaft 114 can further define the second threaded portion 117b that can be adjacent to the distal end 128, and the unthreaded portion 119 between the first and second threaded portions 117a and 117b along the central anchor axis. The electrical stimulation anchors 111 can further include a tip 136 that is disposed at the distal end 128. In an example, as shown, the tip 136 can define the second threaded portion 117b. The tip 136 can be opposite the head 112 along the central anchor axis 125. The shaft 114 can connect the head 112 to the tip 136. The proximal end 130 and the distal end 128 can define opposite outermost ends of the electrical stimulation anchor 111. The first and second electrodes 132 and 134 can be composed of electrically conductive material, for instance titanium, stainless steel, or alloys thereof, so as to transfer electrical current. In an example, the head 112 and the tip 136 can be composed of electrically conductive material, for instance titanium, stainless steel, or allows thereof, so as to transfer electrical current. In an example, the shaft 114 and the tip 136 can define the second electrode 134.

Figure 3C:
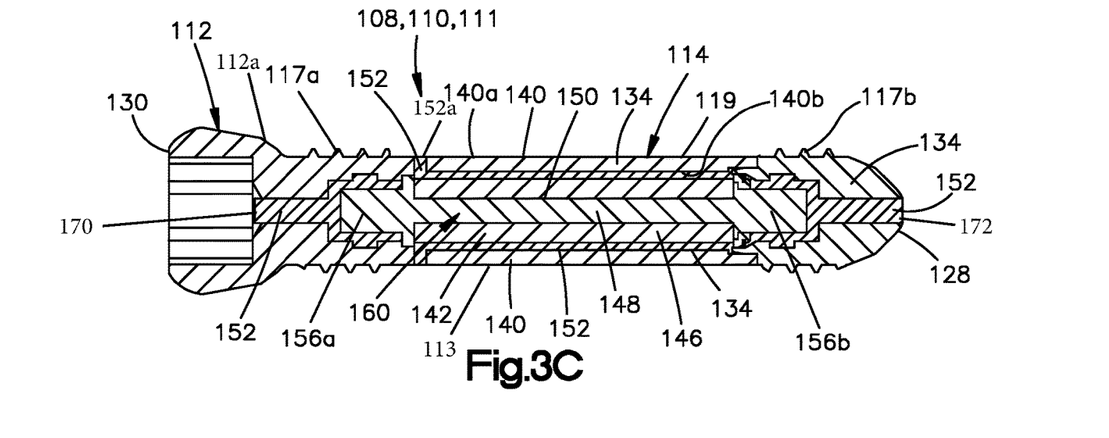
FIG. 3C is a cross section of the electrical stimulation anchor depicted in FIGS. 3A and 3B.
Figure 3D:
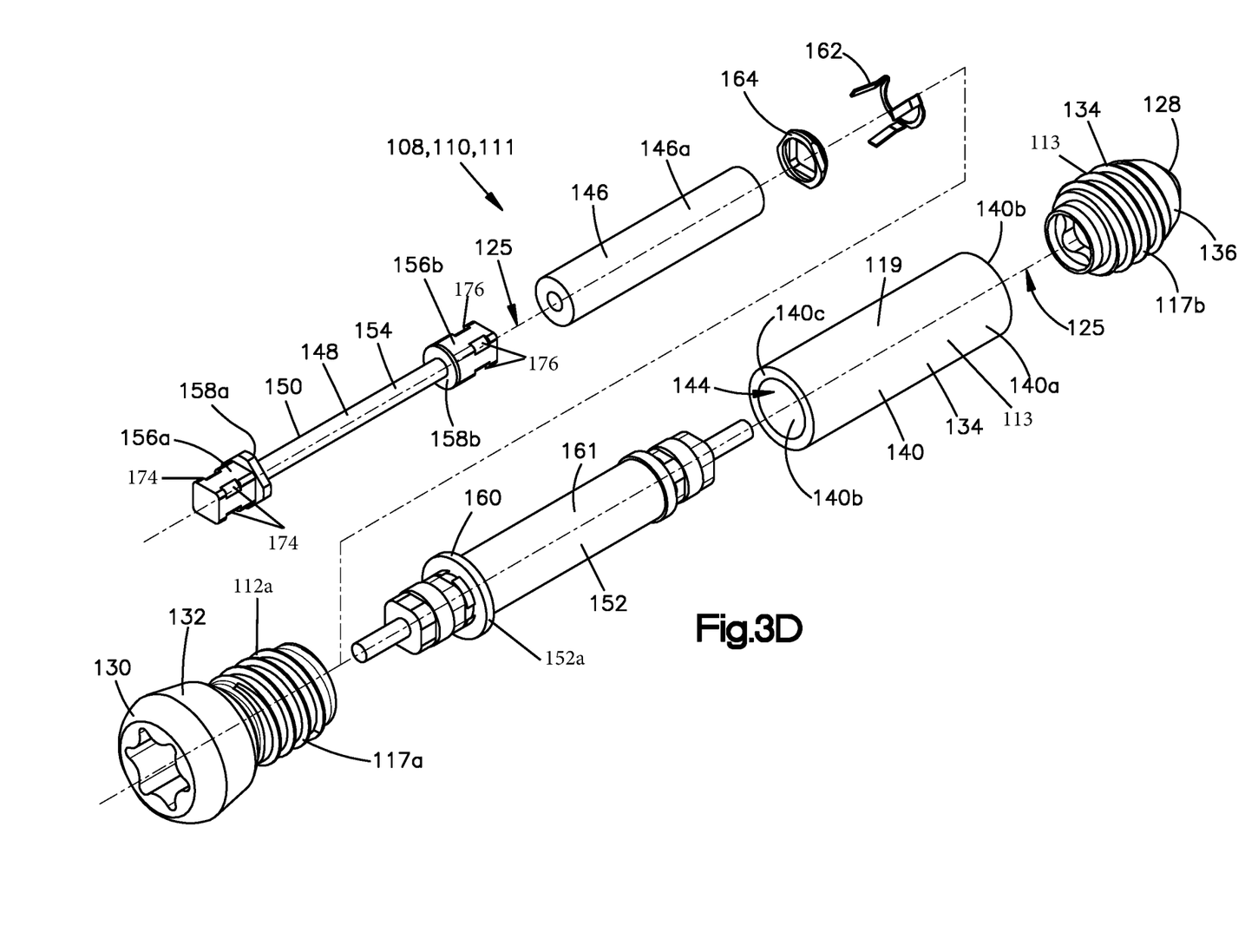
FIG. 3D is an exploded view of the electrical stimulation anchor depicted in FIGS. 3A to 3C.

Referring in particular to FIGS. 3C and 3D, the head 112 can define a cavity 170. In an example, epoxy is injected into the cavity 170 so as to form an electrical insulator 152. The tip 136 can define a cavity 172. In an example, epoxy is injected into the cavity 172 so as to form the electrical insulator 152. The core proximal end 156a can further define at least one, for instance two or more, for instance four, under cut surfaces 174. The head 112, in particular the cavity 170, can define a surface configured to press-fit with the core proximal end 156a, in particular the under cut surfaces 174, so as to be configured to transfer torque applied to the head 112 about the central anchor axis, to the core 148. Similarly, the core distal end 156b can define at least, for instance two or more, for instance four, under cut surfaces 176. The tip 136, in particular the cavity 172, can define a surface configured to press-fit with the core distal end 156b, in particular the under cut surfaces 176, so as to be configured to transfer torque applied to the core 148 about the central anchor axis 125, to the tip 136. Thus, torque can be transferred from the head 112 to the tip 136 by the core 148.

Referring again to FIG. 2, the implant 106 can include an electrical conductor configured to electrically couple the first electrode 132 of the first electrical stimulation anchor 111a with the first electrode 132 of the second electrical stimulation anchor 111b when the implant 106 is secured to the bone 104. It will be understood that at least a portion, up to all, of the implant 106 can be composed of an electrical conductor for instance titanium, stainless steel, or alloys thereof, so as to transfer electrical current between the first electrode 132 of the first electrical stimulation anchor 111a and the first electrode 132 of the second electrical stimulation anchor 111b, thereby creating a short circuit between the proximal ends of 130 of the first and second electrical stimulation anchors 111a and 111b. The implant 106 can include the electrical conductor and can otherwise be made from any suitable biocompatible material, including a metal such as titanium, stainless steel, or alloys thereof, or any suitable alternative implantable material, such as polymers based materials like poly-ether-ether-ketone (PEEK), or PEKK as desired. The material can also be a bio-resorbable material in certain examples.

Figure 4A:
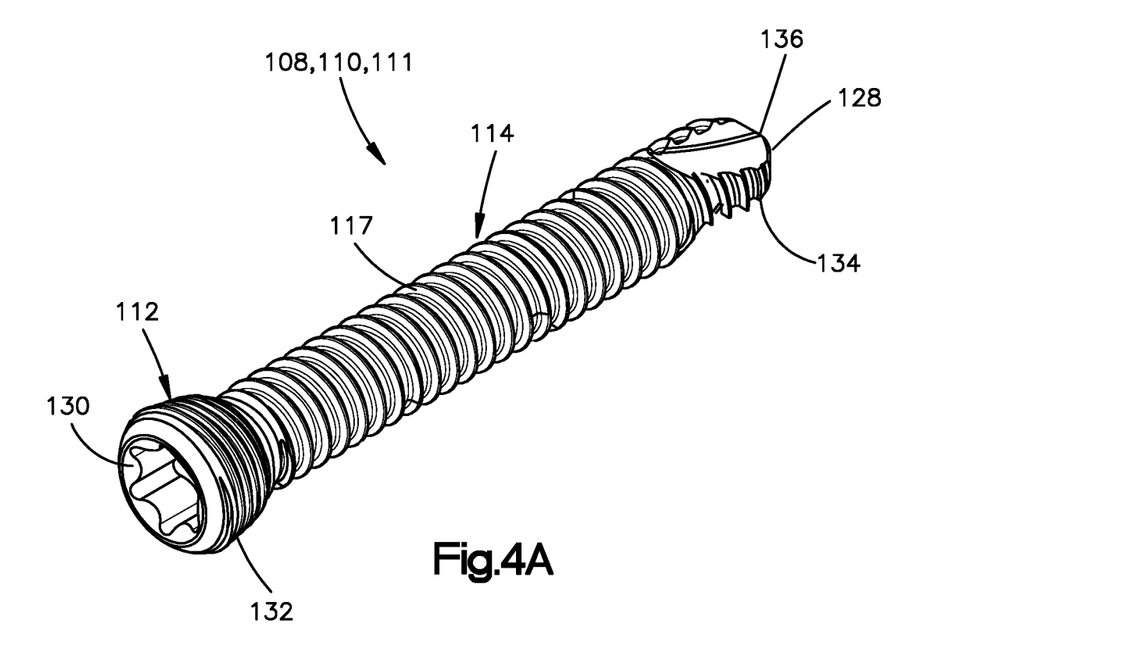
FIG. 4A is a perspective view of the electrical stimulation anchor in accordance with another example embodiment.

Referring also FIGS. 3A and 4A, each of the proximal ends 130 and each of the distal ends 128 can define a respective terminal end of the respective electrical stimulation anchor 111. The first electrical stimulation anchor 111a can define a first length from its proximal end 130 to its distal end 128. The second electrical stimulation anchor 111b can define a second length from its proximal end 130 to its distal end 128 that is substantially equal to the first length of the first electrical stimulation anchor 111a. The term "substantially" as used herein takes into account manufacturing tolerances and movement that does not alter the nature of fixation to the underlying anatomical structure. It will be understood that the first and second lengths of the first and second electrical stimulation anchors 111a and 111b, respectively, can vary as desired. Further, as shown, the bone implant system 100 can include bone anchors 108 that are not configured as electrical stimulation anchors 111. These bone anchors can have the same length as the first and second electrical stimulation anchors 111a and 111b. Alternatively, the bone anchors 108 can be shorter or longer than the first and second lengths of the first and second electrical stimulation anchors 111a and 111b.

The electrical stimulation anchor 111 can be elongate from the proximal end 130 to the distal end 128. For instance, the screw can be substantially elongate along the central anchor axis 125 that extends from the proximal end 130 to the distal end 128. It will be appreciated that the central anchor axis 125 of the electrical stimulation anchor 111 can be straight or curved. Thus, the shaft 114 can be straight or curved as it extends along the central anchor axis 125 from the head 112 to the tip 136.

Referring in particular to FIGS. 3C and 3D, the shaft 114 can include a shaft body 140 and an electrical coil assembly 142 disposed within the shaft body 140. The shaft body 140 can include an outer surface 140a and an inner surface 140b opposite the outer surface 140a. For example, the shaft body 140 can define a cavity 144 within which a portion or all of the electrical coil assembly 142 can be disposed. The second electrically conductive outer surface 113 defined by the second electrode 134 can include at least a portion, for instance all, of the outer surface 140a of the shaft body 140. The tip 136 can also define a portion of the second electrically conductive outer surface 113. In an example, the shaft 114 and the tip 136 can define the second electrode 134 that defines the second electrically conductive outer surface 113.

Figure 4B:
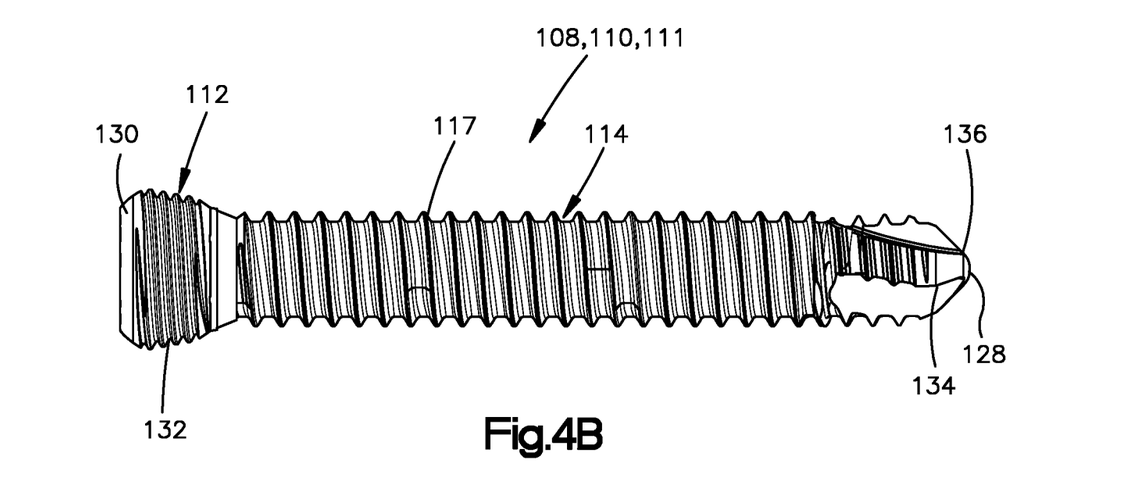
FIG. 4B is a side elevation view of the electrical stimulation anchor depicted in FIG. 4A.
Figure 4C:
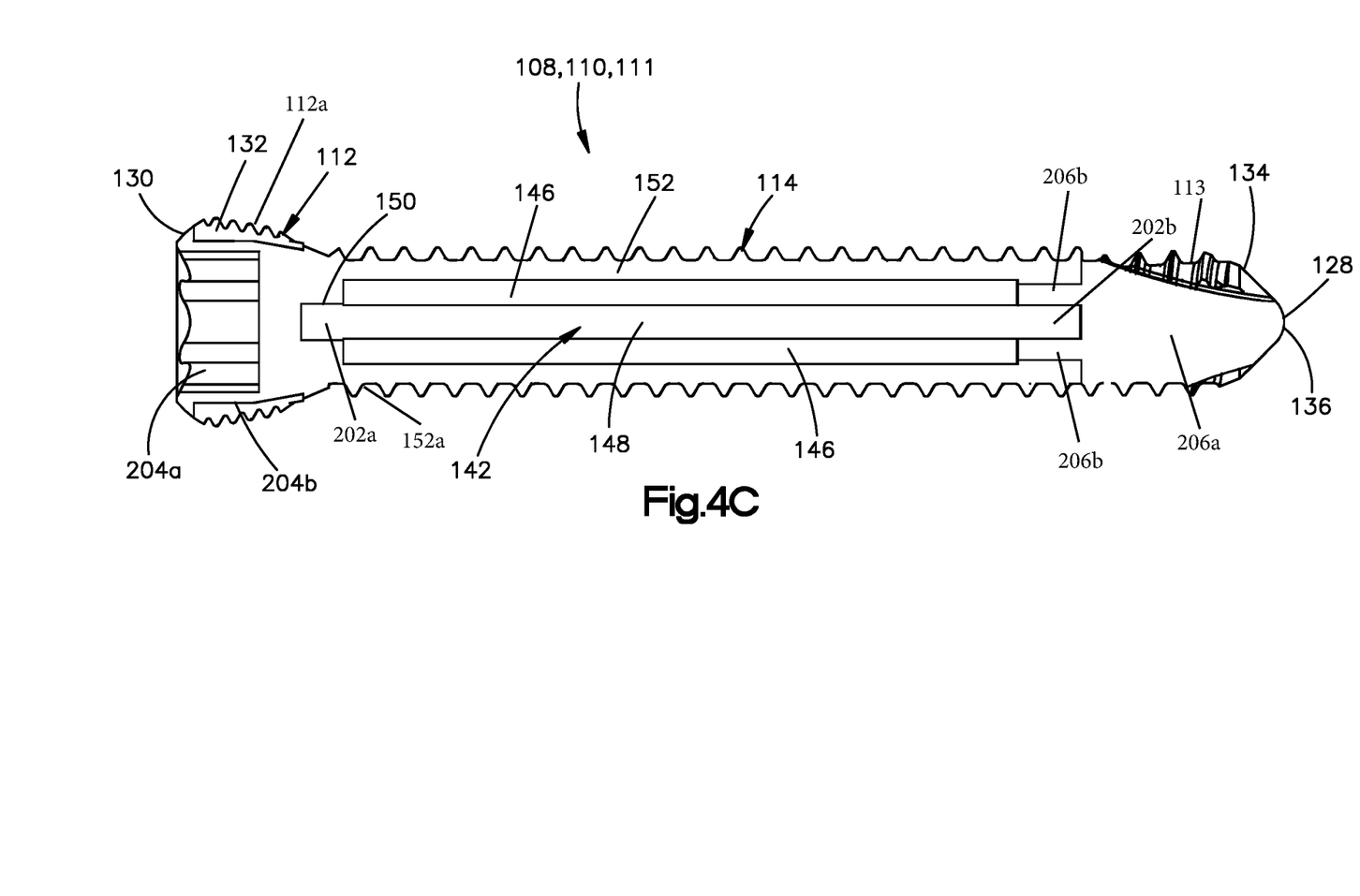
FIG. 4C is a cross section of the electrical stimulation anchor depicted in FIGS. 4A and 4B.
Figure 4D:
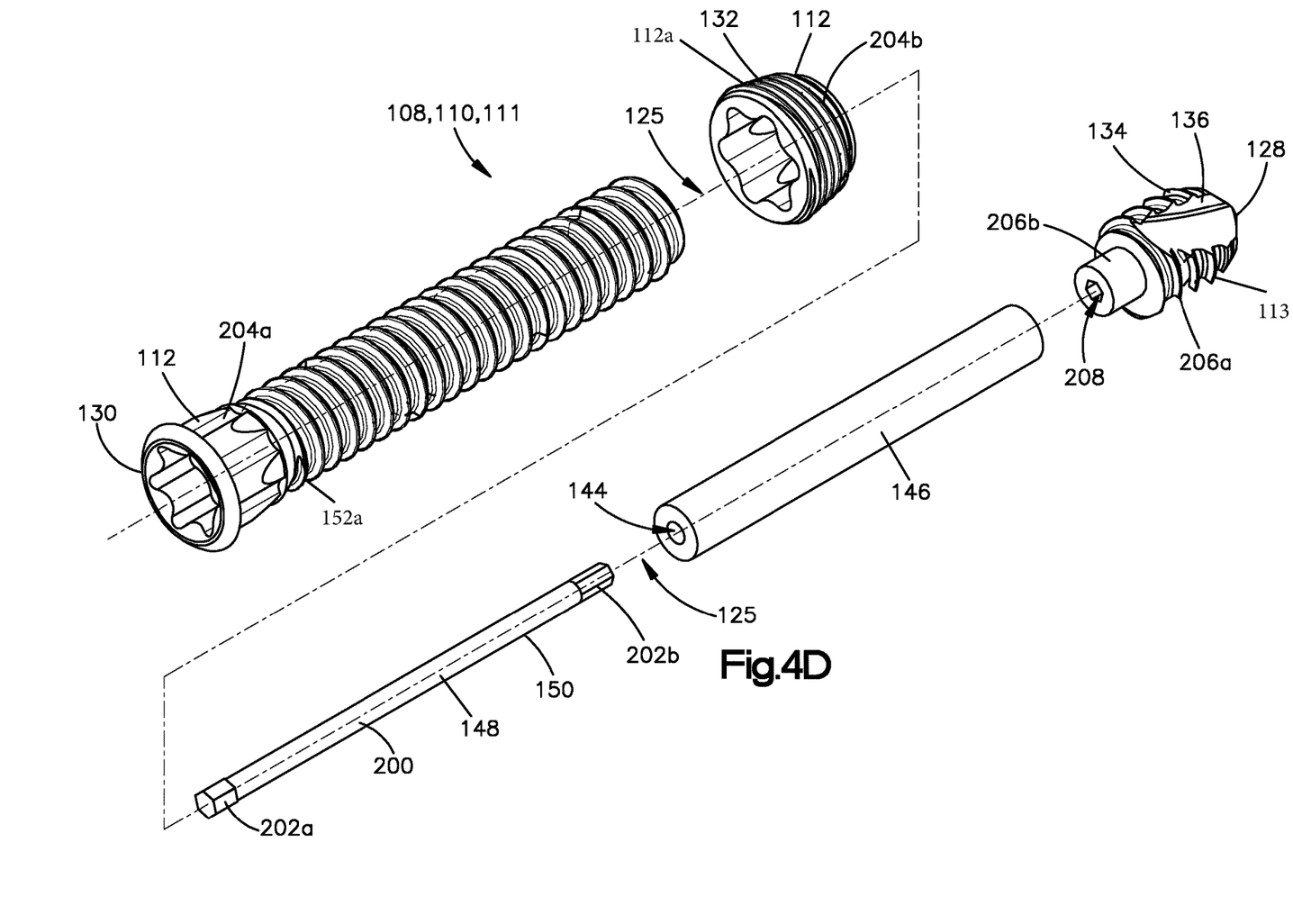
FIG. 4D is an exploded view of the electrical stimulation anchor depicted in FIGS. 4A to 4C.

Referring also to FIGS. 4C and 4D, the electrical coil assembly 142 can include a ferromagnetic core 148 and an electrical coil 146 arranged, for instance wound, about the ferromagnetic core 148. The coil 146 can include an electrically conductive wire that can be wound around the ferromagnetic core 148. In an example, the electrically conductive wire can be wound about the central anchor axis 125. The ferromagnetic core 148 can define an external surface 150, such that the electrically conductive wire, and thus the coil 146, abuts the external surface 150. In an example, with reference to FIG. 2, the first electrical stimulation anchor can include the electrical coil 146 wound around the ferromagnetic core 148 in a first direction, and the second electrical stimulation anchor 111b can include the electrical coil 146 wound around the ferromagnetic core 148 in a second direction that is opposite the first direction. In an example, the first direction is one of clockwise or counterclockwise, and the second direction is the other of clockwise or counterclockwise. Thus, the second electrode 134 of the first electrical stimulation anchor 111a and the second electrode 134 of the second electrical stimulation anchor 111b can be configured to respond to a magnetic field so as to have opposite polarities as each other.

Referring in particular to FIGS. 3C, 3D, 4C, and 4D, the electrical stimulation anchors 111, in particular the shaft 114, can define the electrical insulator 152. The electrical coil 146 and the ferromagnetic core 148 can be disposed within the electrical insulator 152. Thus, the first and second electrical stimulation anchors 111a and 111b can each include the electrical insulator 152, and the respective electrical coils 146 of the first and second electrical stimulation anchors 111a and 111b can be disposed inside the respective electrical insulator 152. The electrical insulator 152 can be composed of an injected molded polymer in certain examples. The electrical insulator 152 can disposed between the first electrically conductive outer surface 112a of the first electrode 132 and the second electrically conductive outer surface 113 of the second electrode 134 along the central anchor axis 125. In particular, the electrical insulator 152 can define an insulator or non-conductive outer surface 152a disposed between the first and second electrically conductive outer surfaces 112a and 113, respectively, along the central anchor axis 125, so as to separate the first electrode 132 and the second electrode from each other. The insulator outer surface 152a can be disposed proximate to the head 112. The insulator outer surface 152a can extend around the central anchor axis 125. For example, the insulator outer surface 152a can be centered around the central anchor axis 125. The insulator outer surface 152a can be configured to be disposed proximate to the inner plate surface 118 of the implant 106 when the implant is secured to the bone 104.

Referring now to the example illustrated in FIGS. 3A-D, the core 148 can define a core body 154 and a core proximal end 156a disposed at a first end of the core body 154. The core proximal end 156a can be attached to the head 112, so as to be configured to transfer torque applied to the head 112 about the central anchor axis 125, to the shaft 114. The core 148, for instance the core proximal end 156a, can be attached to the head 112 of the electrical stimulation anchor 111, for instance by a press-fit, so as to mechanically connect the electrical core assembly 142 with the head 112. For example, the core proximal end 156a can extend outward from the central anchor axis 125 with respect to the core body 154. The core proximal end 156a can be disposed within the electrical insulator 152.

The core 148 can further define a core distal end 156b disposed at a second end of the core body 154 that is opposite the first end of the core body 154 along the central anchor axis 125. The core 148, for instance the core distal end 156b, can be attached to the tip 136 so as to be configured to transfer torque applied to the shaft 114 about the central anchor axis 125, to the tip 136. Thus, torque applied to the head 112 can be transferred to the core 148, which in turn can transfer the torque to the tip 136. The core 148, for instance the core distal end 156b, can be attached to the tip 136 of the electrical stimulation anchor 111, for instance by press-fit, so as to mechanically connect the electrical coil assembly 142 with the tip 136. The core distal end 156b can extend outward from the central anchor axis 125 with respect to the core body 154.

Still referring to FIGS. 3A-D, the core proximal end 156a can further include a proximal surface 158a that faces the distal end 128 of the electrical stimulation anchor 111. The core distal end 156b can further include a distal surface 158b that faces the proximal end 130 of the electrical stimulation anchor. Thus, the proximal surface 158a and the distal surface 158b can face opposite directions as each other along the central anchor axis 125. For instance, the distal surface 158b can face the proximal surface 158a. The proximal surface 158a, distal surface 158b, and the core body 154 can support the coil 146. The coil 146 can be wound from the proximal surface 158a, to the distal surface 158b, on the external surface 150 and about the central anchor axis 125. The coil 146 can be wound in a clockwise or counterclockwise direction. The external surface 150 of the core body 154 can extend from the proximal surface 158a to the distal surface 158b.

The electrical insulator 152 can include an insulator proximal end 160 that can support the shaft body 140. The insulator proximal end 160 can define the insulator outer surface 152a. The electrical insulator 152 can include an insulator body 161 that can be disposed within the cavity 144 of the shaft body 140. The insulator proximal end 160 can extend outward from the central anchor axis 125 with respect to the insulator body 161, such that the insulator outer surface 152a defines a portion of the outer surface of the electrical stimulation anchor 111. The shaft body 140 can be electrically conductive so as to define at least a portion of the second electrode 134. The insulator proximal end 160 can extend outward from the central anchor axis 125 a distance that is greater than the insulator body extends outward from the central anchor axis 125. Thus, the insulator proximal end 160 can separate the shaft body 140 from the head 112, such that the shaft body 140 and the head 112 do not contact each other. Thus, the insulator proximal end 160, in particular the insulator outer surface 152a of the insulator proximal end 160, can be disposed between head 112 and the shaft 114 so as to electrically separate the first electrode 132 and the second electrode 134 from each other. Further, the outer surface 140a of the shaft body 140 can define the unthreaded portion 119. Thus, the shaft body 140 can be disposed between the first threaded portion 117a and the second threaded portion 117b along the central anchor axis 125. The shaft body 140 can be attached or can be monolithic with the tip 136. The shaft body 140 can also define a proximal shaft body end 140c and a distal shaft body end 140d opposite the proximal shaft body end 140c along the central anchor axis 125. The proximal shaft body end 140c can abut the insulator proximal end 160, and the distal shaft body end 140d can be attached to the tip 136, so as to electrically couple the shaft body and the tip 136.

With continuing reference to FIGS. 3C and 3D, the shaft 114, in particular the electrical coil assembly 142, can further include an electrically conductive clip 162 in contact with the shaft body 140, in particular the inner surface 140b of the shaft body 140. The clip 162 can also be in contact with the coil 146, in particular an outer surface 146a of the coil 146, so as to electrically couple the coil 146 with the shaft body 140, and thus the coil 146 with the second electrode 134. The shaft 114 can also include a placeholder 164 that is disposed at an end of the coil 146 adjacent to the distal shaft body end 140d. The placeholder 164 can be disposed so as to prevent the clip 162 from contacting the core 148.

In an example manufacturing process, the electrical coil 146 can be wound around the ferromagnetic core 148 to define the electrical coil assembly 142. The electrical coil assembly 142 can be inserted into the cavity 144 defined by the shaft body 140 of the electrical stimulation locking anchor 111. The core proximal end 156a can be attached to the head 112, and the core distal end 156b can be attached to the tip 136 that is opposite the head 112 along the central anchor axis 125. The shaft body 140 can be secured to the electrical coil 146, such that electrical current can be transferred between the electrical coil 146 and the shaft body 140. The electrical coil assembly 142 that is attached to the head 112 and the tip 136 can be set in a form, such that the head 112 and the shaft body 140 define a gap therebetween along the central anchor axis 125. A non-conductive polymer can be injected into the cavity 170 defined by the head 112 or the cavity 172 defined by the tip 136, such that the polymer surrounds the electrical coil assembly 142, for example, so as to define the electrical insulator 152. The non-conductive polymer can be injected such that the polymer fills the gap between the head 112 and shaft body 140, so as to define the insulator proximal end 160, and in particular the insulator outer surface 152a, of the electrical insulator 152.

In an example, epoxy is injected at the head 112 to mold the electrical insulator 152 around the coil assembly 142. Before injection molding the electrical insulator 152 in a form, in an example, the electrically conductive portions of the electrical stimulation anchor 111 are positioned in a form or mold. The clip 162 and the placeholder 164 can hold the coil 146 in place relative to the core 148 in the form, so that the electrical coil assembly is centered within the electrical insulator 152 after injection molding insulator material to form the electrical insulator 152 around the electrical coil assembly 142.

Referring now to the example illustrated in FIGS. 4A-D, the core 148 can define a core body 200 and a core proximal end 202a disposed at a first end of the core body 200. The core 148 can further define a core distal end 202b disposed at a second end of the core body 200 that is opposite the first end of the core body 200 along the central anchor axis 125. The core proximal end 202a can be disposed within the electrical insulator 152. The core proximal end 202a can be disposed outside of the coil 146, such that the core proximal end 202a extends from the cavity 144 along the central anchor axis. Similarly, the core distal end 202b can be disposed within the electrical insulator 152. The core distal end 202b can also be disposed outside of the coil 146, such that the core distal end 202b extends from the cavity 144 along the central anchor axis. The core proximal end 202a can be attached to the head 112, for instance by a press-fit, so as to mechanically connect the electrical core assembly 142 with the head 112. For example, the core proximal end 202a can define a hexagonal shape, so as to be received in a press-fit with the head 112. It will be understood that the core proximal end 202a can be alternatively shaped as desired. For example, the core proximal end 202a can extend outward from the central anchor axis 125 with respect to the core body 200.

The core distal end 202b can be attached to the tip 136 of the electrical stimulation anchor 111, for instance by press-fit, so as to mechanically connect the electrical coil assembly 142 with the tip 136. For example, the core distal end 202b can define a hexagonal shape, so as to be received in a press-fit with the head 112. It will be understood that the core distal end 202b can be alternatively shaped as desired. For example, the core distal end 202b can extend outward from the central anchor axis 125 with respect to the core body 200. The coil 146 can be wound from the core proximal end 202a, to the core distal end 202b, on the external surface 150 and about the central anchor axis 125. The coil 146 can be wound in a clockwise or counterclockwise direction. The external surface 150 of the core body 200 can extend from the core proximal end 202a to the core distal end 202b. The core body 200 can define a cylinder, though it will be understood that the core body 200 can be alternatively shaped as desired.

Referring in particular to FIG. 4C, the head 112 can include an insulative portion 204a and an electrically conductive portion 204b. In an example configuration, the electrically conductive portion 204b can fit around the insulative portion 204a, such that the electrically conductive portion 204b is configured to contact the electrical conductor of the plate 116 when the electrical stimulation anchor 111 secures the implant 106 to the bone 104. The electrically conductive portion 204b of the head 112 can also be electrically connected to the coil 146, for instance via a wire or other electrically conductive member, such that the head 112 is configured to transfer electrical current between the coil 146 and the electrical conductor of the plate 116 when the electrical stimulation anchor 111 secures the implant 106 to the bone 104. The tip 136 can include a body 206a and a member 206b connected to the body 206a. The member 206b can extend from the body along the central anchor axis 125. The member 206b can be electrically conductive and can abut the coil 146, so as to electrically couple the coil 146 with the tip 136, and thus the second electrode 134. The member 206b can define a cavity 208 that is sized to receive the core distal end 202b, so that the core 148 can contact the member 206b, thereby establishing another electrical connection between the coil 146 and the tip 136. The cavity 208b can be centered about the central anchor axis 125. Referring to FIGS. 4A and 4B, in an example, the epoxy of at least a portion of the shaft 114 is coated with an electrically conductive material, such as titanium. Thus, the shaft 114 and the tip 136 can be electrically coupled so as to define the second electrode 134, and thus the second electrically conductive outer surface 113. In an example, by coating at least a portion of the shaft 114 from the tip 136 to a location proximate to the head 112 along the central anchor axis with the electrically conductive material, the surface area of the insulative outer surface 152a can be reduced, and the insulative outer surface 152a can be disposed proximate to the head 112. Referring in particular to FIG. 4C, in an example in which the shaft 114 is not coated with an electrically conductive material, the first electrode 132 can be disposed at the head 112, and the second electrode 134 can be disposed at the tip 136.

In operation, referring also to FIG. 2, the bone implant system 100 is exposed to a magnetic field that is generated by the PEMF device 102, so as to generate an electric field between the first and second electrical stimulation anchors 111a and 111b. The magnetic field generated by the PEMF device 102 can be a dynamic field that induces an electric current in the electrical coils 146 of the first and second electrical stimulation anchors 111a and 111b. In particular, the PEMF device 102 can include one or more coils that can function as a primary coil, and the coils 146 can function as secondary coils when exposed to the magnetic field generated by the primary coil of the PEMF device 102. The electric coil 146 of the first electrical stimulation anchor 111a can be wound in a direction that is opposite the direction in which the coil 146 of the second electrical stimulation anchor 111b is wound. Thus, the second electrode 134 of the first electrical stimulation anchor 111a can have a polarity that is opposite the polarity of the second electrical stimulation anchor 111b. Thus, for example, the first and second electrical stimulation anchors 111a and 111b can be configured to respond to a magnetic field so as to generate an electric field from the distal end 128 of one of the first and second electrical stimulation anchors 111a and 111b to the distal end 128 of the other of the first and second electrical stimulation anchors 111a and 111b.

As described above, the plate 116 can electrically connect the first electrode 132 of the first electrical stimulation locking anchor 111a with the first electrode 132 of the second electrical stimulation locking anchor 111b. It is recognized herein that this configuration can increase the predictability and reliability of the electric field that is generated by the first and second electrical stimulation anchors 111a and 111b. Without being bound by theory, it is further recognized herein that this arrangement that includes the electrical stimulation locking anchors 111 having the insulative outer surface 152a disposed proximate to the head 112 can strengthen the electric field as compared to an electric field that is generated between anchors having the same polarity as each other. It is further recognized herein that this arraignment that includes the electrical stimulation locking anchors 111 having the insulator outer surface 152a disposed proximate to the head 112 can strengthen the electric field as compared to the same arrangement with different locking anchors that have an outer insulative portion disposed closer to the tip 136 as compared to the insulative outer surface 152a of the electrical stimulation locking anchors 111. Thus, it is recognized herein that adjacent electrical stimulation locking anchors that are secured to an implant and that have first and second electrodes separated at a location proximate to the head 112 can strengthen the electric field as compared to adjacent electrical stimulation anchors that are secured to an implant and that have first and second electrodes disposed proximate to the tip. Having the first and second electrodes disposed proximate to the head 112 can, in some cases, reduce the mechanical strength of the anchor, such that the anchor cannot be configured to function as a locking anchor. Without being bound by theory, it is also recognized herein that the above-described electrical stimulation locking anchors 111 are configured for electrical stimulation while maintaining the mechanical strength required to function as a locking screw, so as to transfer torque about the central anchor axis 125 from the head 112 to the tip 136. Further still, it is recognized herein that the ferromagnetic core 148 can strengthen the electric field that is generated as compared to an electrical coil assembly without the ferromagnetic core 148.

In response to the magnetic field generated by the PEMF device 102, by way of example, a current can be induced in the coil 146 of the first electrical stimulation anchor 111a from the proximal end 130 to the distal end 128 of the first electrical stimulation anchor 111a, and the current can be induced in the coil 146 of the second electrical stimulation anchor 111b from the distal end 128 to the proximal end 130. Thus, the electrical field generated by the induced currents can be strengthened, so as to better treat a fracture.

Referring to FIGS. 3A-D, the induced current can be transferred from the coil 146 to the shaft body 140, and thus the second electrode 134, via the clip 162. Similarly, referring to FIGS. 4A-D, the induced current can be transferred directly from the electrical coil 146 to the tip 136, and thus the second electrode 134. The first and second electrical stimulation anchors 111a and 111b can each define the respective electrical insulator that can be disposed between the first electrode 132 and the second electrode 134, such that electrical current induced by the magnetic field is not transferred from the first electrode 132 to the second electrode 134. Further, the electrical coil 146 of the first electrical stimulation anchor can be electrically connected to the second electrode 134 of the first electrical stimulation anchor 111a, and the electrical coil 146 of the second electrical stimulation anchor 111b can be electrically connected to the second electrode 134 of the second electrical stimulation anchor 111b.

Thus, as described above, a method for treating a fracture in a bone can include positioning a bone plate over the bone, such that the fracture is disposed between a first bone fixation hole and a second bone fixation hole along a longitudinal direction. The method can further include inserting a first electrical stimulation anchor into the first bone fixation hole, and inserting a second electrical stimulation anchor into the second bone fixation hole. Further still, the method can include causing an electrical field to be generated between the first and second electrical stimulation anchors. In some cases, causing the electrical field to be generated includes exposing the bone plate to a magnetic field, so as to induce an electrical current in the first electrical stimulation anchor and the second electrical stimulation anchor. The first electrical stimulation anchor can include a first coil wrapped in a first direction, and the second electrical stimulation anchor includes a second coil wound in a second direction opposite the first direction. In some examples, the method for treating the fracture includes connecting a proximal end of the first electrical stimulation anchor to an electrical conductor of the bone plate, and connecting a proximal end of the second electrical stimulation anchor to the electrical conductor of the bone plate, so as to electrically couple the proximal end of the first electrical stimulation anchor with the proximal end of the second electrical stimulation anchor. Causing the electrical field to be generated can also include exposing the first electrical stimulation anchors to a magnetic field so as to induce a first electrical current from the proximal end of the first electrical stimulation anchor to a distal end of the first electrical stimulation anchor that is opposite the proximal end, and exposing the second electrical stimulation anchor to the magnetic field so as to induce a second electrical current from a distal end of the second electrical stimulation anchor to the proximal end of the second electrical stimulation anchor, wherein the distal end of the second electrical stimulation anchor is opposite the proximal end of the second electrical stimulation anchor.

While the techniques described herein can be implemented and have been described in connection with the various embodiments of the various figures, it is to be understood that other similar embodiments can be used or modifications and additions can be made to the described embodiments without deviating therefrom. For example, it should be appreciated that the steps disclosed above can be performed in the order set forth above, or in any other order as desired. Further, one skilled in the art will recognize that the techniques described in the present application may apply to any environment, whether wired or wireless, and may be applied to any number of such devices connected via a communications network and interacting across the network. Therefore, the techniques described herein should not be limited to any single embodiment, but rather should be construed in breadth and scope in accordance with the appended claims.

What is claimed:

1. An electrical stimulation anchor configured to lock to a bone implant so as to secure the bone implant to a bone, the electrical stimulation anchor comprising:
    a head configured to lock to the bone implant, the head includes a head body that defines a first electrode that defines a first electrically conductive outer surface;
    a tip opposite the head along a central anchor axis that extends along a direction;
    a shaft that is elongated along the central anchor axis and connects the head to the tip, the shaft and the tip defining a second electrode that defines a second electrically conductive outer surface, wherein the head is configured to receive a torque that is transferred to the shaft;
    a core assembly including a ferromagnetic core and an electrical coil wound around the ferromagnetic core, wherein the ferromagnetic core extends into the head; and
    an electrical insulator defining a non-conductive outer surface disposed between the first electrically conductive outer surface and the second electrically conductive outer surface along the direction so as to separate the first electrode and the second electrode from each other, the non-conductive outer surface disposed closer to the head along the central anchor axis as compared to the tip,
    wherein the electrical insulator is further disposed in a cavity of the head so as to surround the ferromagnetic core in the head, and
    wherein the shaft includes a shaft body that at least partially defines the second electrically conductive outer surface, the shaft body is rotatably fixed to the head body, and the electrical insulator separates the head body from the shaft body along the direction.

2. The electrical stimulation anchor as recited in claim 1, wherein the non-conductive outer surface is proximate to the head and extends around the central anchor axis.

3. The electrical stimulation anchor as recited in claim 2, wherein the non-conductive outer surface is centered around the central anchor axis.

4. The electrical stimulation anchor as recited in claim 1, wherein the ferromagnetic core defines a core body and a core proximal end that is attached to the head so as to be configured to transfer the torque applied to the head about the central anchor axis, to the shaft.

5. The electrical stimulation anchor as recited in claim 4, wherein the core proximal end extends radially outward from the central anchor axis with respect to the core body.

6. The electrical stimulation anchor as recited in claim 4, wherein the ferromagnetic core further defines a core distal end opposite the core proximal end along the central anchor axis, wherein the core distal end is attached to the tip so as to be configured to transfer torque applied to shaft about the central anchor axis, to the tip.

7. The electrical stimulation anchor as recited in claim 6, wherein the core distal end extends radially outward from the central anchor axis with respect to the core body.

8. A bone implant kit comprising:
    an implant defining 1) an inner surface configured to face a bone to which the bone implant kit is configured to be attached, 2) an outer surface opposite the inner surface, 3) a first internal surface that extends from the inner surface to the outer surface so as to define a first bone fixation hole, and 4) a second internal surface that extends from the inner surface to the outer surface so as to define a second bone fixation hole spaced from the first bone fixation hole along a longitudinal direction;

a first electrical stimulation anchor of claim 1, the first electrical stimulation anchor sized and configured for insertion into the first bone fixation hole so as to threadedly mate with the first internal surface, the first electrical stimulation anchor including a first electrical coil wound around a first ferromagnetic core in a first direction; and a second electrical stimulation anchor of claim 1, the second electrical stimulation anchor sized and configured for insertion into the second bone fixation hole so as to threadedly mate with the second internal surface, the second electrical stimulation anchor including a second electrical coil wound around a second ferromagnetic core in a second direction opposite the first direction, wherein the first and second electrical stimulated anchors are configured to secure the implant to the bone such that the inner surface of the implant is spaced from the bone, and the first and second electrical stimulation anchors are configured to respond to a magnetic field so as to generate an electric field between the first and second electrical stimulated anchors.

9. The bone implant kit as recited in claim 8, wherein the first and second bone fixation holes are spaced from each other along the longitudinal direction, and the implant is configured to be positioned over the bone such that the first and second bone fixation holes are disposed on opposite sides of a fractured portion of the bone.

10. The bone implant kit as recited in claim 9, wherein the first and second electrical stimulation anchors are configured to respond to the magnetic field so as to generate the electric field at the fractured portion of the bone.

11. The electrical stimulation anchor as recited in claim 1, wherein the ferromagnetic core extends into the head along the central axis.

12. The electrical stimulation anchor as recited in claim 1, wherein the electrical insulator further extends into a cavity of the shaft so as to be disposed radially between the shaft and the electrical coil.

13. The electrical stimulation anchor as recited in claim 1, wherein the electrical insulator further extends into a cavity of the tip so as to surround the core in the tip.

14. The electrical stimulation anchor as recited in claim 1, wherein the electrically non-conductive outer surface is aligned with a radially outer surface of the shaft along the direction.

15. The electrical stimulation anchor as recited in claim 1, wherein the shaft body defines a first part of the second electrically conductive outer surface and the tip defines a second part of the second electrically conductive outer surface.

16. An electrical stimulation anchor configured to lock to a bone implant so as to secure the bone implant to a bone, the electrical stimulation anchor comprising:

a head configured to lock to the bone implant, the head defining a first electrode that defines a first electrically conductive outer surface;

a tip opposite the head along a central anchor axis that extends along a direction;

a shaft that is elongated along the central anchor axis and connects the head to the tip, the shaft and the tip defining a second electrode that defines a second electrically conductive outer surface, wherein the head is configured to receive a torque that is transferred to the shaft;

a core assembly including a ferromagnetic core and an electrical coil wound around the ferromagnetic core, wherein the ferromagnetic core extends into the head; and an electrical insulator defining a non-conductive outer surface disposed between the first electrically conductive outer surface and the second electrically conductive outer surface along the direction so as to separate the first electrode and the second electrode from each other, the non-conductive outer surface disposed closer to the head along the central anchor axis as compared to the tip, wherein the electrical insulator is further disposed in a cavity of the head so as to surround the ferromagnetic core in the head, wherein the ferromagnetic core defines a core body and a core proximal end that is attached to the head so as to be configured to transfer the torque applied to the head about the central anchor axis, to the shaft, wherein the ferromagnetic core further defines a core distal end opposite the core proximal end along the central anchor axis, wherein the core distal end is attached to the tip so as to be configured to transfer torque applied to shaft about the central anchor axis, to the tip, and wherein:
the core proximal end defines a proximal surface;
the core distal end defines a distal surface that faces the proximal surface; and
the electrical coil is supported by the proximal surface, the distal surface, and the core body.

17. The electrical stimulation anchor as recited in claim 16, wherein the head includes a head body that defines the first electrically conductive outer surface and the shaft includes a shaft body that defines the second electrically conductive outer surface, wherein the shaft body is rotatably fixed to the head body and separated from the head body along the direction by the electrical insulator.

18. The electrical stimulation anchor as recited in claim 16, wherein the core proximal end extends radially outward from the central anchor axis with respect to the core body.

19. An electrical stimulation anchor configured to lock to a bone implant so as to secure the bone implant to a bone, the electrical stimulation anchor comprising:

a head configured to lock to the bone implant, the head defining a first electrode that defines a first electrically conductive outer surface;

a tip opposite the head along a central anchor axis that extends along a direction;

a shaft that is elongated along the central anchor axis and connects the head to the tip, the shaft and the tip defining a second electrode that defines a second electrically conductive outer surface, wherein the head is configured to receive a torque that is transferred to the shaft;

a core assembly including a ferromagnetic core and an electrical coil wound around the ferromagnetic core, wherein the ferromagnetic core extends into the head; and an electrical insulator defining a non-conductive outer surface disposed between the first electrically conductive outer surface and the second electrically conductive outer surface along the direction so as to separate the first electrode and the second electrode from each other, the non-conductive outer surface disposed closer to the head along the central anchor axis as compared to the tip, wherein the electrical insulator is further disposed in a cavity of the head so as to surround the ferromagnetic core in the head, and wherein a radially outermost surface of the head defines the first electrically conductive outer surface, wherein radially outermost surfaces of the shaft and tip define the second electrically conductive outer surface, and wherein the non-conductive outer surface is contiguous with the first electrically conductive outer surface and the second electrically conductive outer surface.

20. The electrical stimulation anchor as recited in claim 19, wherein the ferromagnetic core defines a core body and a core proximal end that is attached to the head so as to be configured to transfer the torque applied to the head about the central anchor axis, to the shaft.

* * * * *